(12) United States Patent
Kim

(10) Patent No.: US 11,045,299 B2
(45) Date of Patent: Jun. 29, 2021

(54) IMPLANT FOR TISSUE LIFTING

(76) Inventor: Jong Woo Kim, Incheon (KR)

(*) Notice: Subject to any disclaimer, the term of this patent is extended or adjusted under 35 U.S.C. 154(b) by 0 days.

(21) Appl. No.: 14/000,775

(22) PCT Filed: Jun. 5, 2012

(86) PCT No.: PCT/KR2012/004421
§ 371 (c)(1),
(2), (4) Date: Aug. 21, 2013

(87) PCT Pub. No.: WO2013/065923
PCT Pub. Date: May 10, 2013

(65) Prior Publication Data
US 2014/0228971 A1    Aug. 14, 2014

(30) Foreign Application Priority Data

Oct. 31, 2011  (KR) .......................... 10-2011-0112135

(51) Int. Cl.
*A61F 2/02*       (2006.01)
*A61L 27/18*     (2006.01)
(Continued)

(52) U.S. Cl.
CPC .......... *A61F 2/02* (2013.01); *A61B 17/06166* (2013.01); *A61F 2/0059* (2013.01);
(Continued)

(58) Field of Classification Search
CPC .... A61B 17/06166; A61B 2017/06176; A61B 2017/00792; A61B 2017/00796;
(Continued)

(56) References Cited

U.S. PATENT DOCUMENTS 6,475,139 B1 * 11/2002 Miller ............... A61B 1/00087
600/135
7,297,102 B2   11/2007 Smith et al.
(Continued)

FOREIGN PATENT DOCUMENTS

CN     201098221 Y    8/2008
CN     101808587 A    8/2010
(Continued)

OTHER PUBLICATIONS

English Translation of CN Office Action for Chinese Application No. 201280016917.1 dated Dec. 31, 2014.
(Continued)

*Primary Examiner* — Katherine H Schwiker
(74) *Attorney, Agent, or Firm* — Novick, Kim & Lee, PLLC; Jae Youn Kim; Jihun Kim

(57) ABSTRACT

Provided is an implant for a tissue lifting that is inserted between sagged or wrinkled skin and subcutaneous muscle to enable pulling and smoothing tissue, wherein the implant for tissue lifting can be inserted between skin and subcutaneous muscle, includes the bioimplantable thread having a distal portion where pulling is required and a proximal portion where the bioimplantable thread is pulled, and the mesh member that is fixedly coupled to the distal portion of the bioimplantable thread and has numerous pores wherein bodily tissues grow and fill the pores.

14 Claims, 10 Drawing Sheets

(51) Int. Cl.
  *A61L 27/16* (2006.01)
  *A61L 27/56* (2006.01)
  *A61L 27/50* (2006.01)
  *A61B 17/06* (2006.01)
  *A61F 2/00* (2006.01)
  *A61B 17/00* (2006.01)

(52) U.S. Cl.
  CPC .............. *A61L 27/16* (2013.01); *A61L 27/18* (2013.01); *A61L 27/50* (2013.01); *A61L 27/56* (2013.01); *A61B 2017/00792* (2013.01); *A61B 2017/06176* (2013.01); *A61F 2250/0051* (2013.01); *A61L 2430/34* (2013.01)

(58) Field of Classification Search
  CPC ........... A61B 2017/00805; A61B 2017/00761; A61B 2017/06171; A61B 2017/0618; A61B 2017/06185; A61B 2017/06057; A61B 2017/0412; A61B 2017/0427; A61F 2250/0051; A61F 2/0059; A61F 2/02; A61F 2/0063; A61F 2/0045; A61F 2/0031; A61F 2/0036; A61F 2002/0068; A61F 2002/0072; A61F 2/005; A61F 2/0054; A61F 2/08; A61F 2/105; A61F 2002/0081; A61F 2002/0086; A61F 2002/009; A61F 2002/0091; A61F 2002/0847; A61F 2002/0852; A61F 2002/0858; A61F 2002/0864; A61F 2002/087
  USPC ........................................... 623/23.72, 23.74
  See application file for complete search history.

(56) References Cited

U.S. PATENT DOCUMENTS

| | | | |
|---|---|---|---|
| 7,601,118 B2 | 10/2009 | Smith et al. | |
| 2002/0143234 A1* | 10/2002 | LoVuolo | A61B 17/06109 600/30 |
| 2004/0231678 A1* | 11/2004 | Fierro | 128/885 |
| 2005/0240224 A1* | 10/2005 | Wu | 606/228 |
| 2005/0267532 A1* | 12/2005 | Wu | A61B 17/06166 606/228 |
| 2006/0025649 A1 | 2/2006 | Smith et al. | |
| 2006/0058892 A1* | 3/2006 | Lesh et al. | 623/23.72 |
| 2007/0038249 A1* | 2/2007 | Kolster | A61B 17/06 606/228 |
| 2007/0156175 A1 | 7/2007 | Weadock et al. | |
| 2007/0173887 A1* | 7/2007 | Sasaki | A61B 17/0401 606/232 |
| 2007/0293892 A1 | 12/2007 | Takasu | |
| 2007/0299300 A1 | 12/2007 | Smith et al. | |
| 2008/0027273 A1 | 1/2008 | Gutterman | |
| 2008/0082113 A1 | 4/2008 | Bishop et al. | |
| 2009/0018655 A1* | 1/2009 | Brunelle et al. | 623/13.19 |
| 2009/0082791 A1 | 3/2009 | Schroeder et al. | |
| 2009/0171143 A1* | 7/2009 | Chu | A61B 17/0401 600/37 |
| 2009/0248071 A1* | 10/2009 | Saint et al. | 606/232 |
| 2010/0025643 A1 | 2/2010 | Hoerold et al. | |
| 2010/0137679 A1* | 6/2010 | Lashinski et al. | 600/37 |
| 2010/0256443 A1 | 10/2010 | Griguol | |
| 2010/0305695 A1 | 12/2010 | Devonec | |
| 2011/0124956 A1* | 5/2011 | Mujwid et al. | 600/30 |
| 2011/0130774 A1* | 6/2011 | Criscuolo et al. | 606/151 |
| 2011/0201876 A1 | 8/2011 | Roll et al. | |
| 2011/0306822 A1* | 12/2011 | Witzmann | A61B 17/0401 600/31 |
| 2012/0232655 A1* | 9/2012 | Lorrison | D03D 3/02 623/13.19 |
| 2015/0216648 A1* | 8/2015 | Beyer | D04B 1/22 606/151 |

FOREIGN PATENT DOCUMENTS

| | | |
|---|---|---|
| JP | 2007-330593 A | 12/2007 |
| JP | 2011-502670 A | 1/2011 |
| KR | 10-2007-0048178 A | 5/2007 |
| KR | 10-0724706 B1 | 6/2007 |
| KR | 10-0745571 B1 | 8/2007 |
| KR | 10-2007-0093256 A | 9/2007 |
| KR | 20-0442490 Y1 | 11/2008 |
| KR | 10-0886757 B1 | 3/2009 |
| KR | 10-2009-0036748 A | 4/2009 |
| KR | 10-2010-0030650 A | 3/2010 |
| KR | 10-2010-0058650 A | 6/2010 |
| KR | 10-2010-0134941 A | 12/2010 |
| KR | 10-2011-0059706 A | 6/2011 |
| KR | 10-1044731 B1 | 6/2011 |
| WO | WO-2005/096956 A1 | 10/2005 |
| WO | 2007111407 A1 | 10/2007 |
| WO | 2009040132 A1 | 4/2009 |
| WO | 2010051506 A1 | 5/2010 |
| WO | 201109483 A1 | 8/2011 |
| WO | 2013122339 A1 | 8/2013 |

OTHER PUBLICATIONS

Supplementary European Search Report for PCT/KR2012004421, dated Feb. 24, 2015.
Australian Examination Report dated Nov. 25, 2014.
International Search Report and Written Opinion (both in Korean with English translation) for PCT/KR2012/004421, dated Dec. 26, 2012; ISA/KR.
English Translation of Notice of Allowance for Korean Priority application 10-2011-0112135, dated May 31, 2012.
Japanese Office Action issued by Japanese Patent Office dated Mar. 31, 2015, which corresponds to the Japanese Patent Application No. 2014-538689, which corresponds to the instant application. (No translation provided.).

* cited by examiner

IMPLANT FOR TISSUE LIFTING

CROSS-REFERENCE TO RELATED APPLICATIONS

This application is a 371 U.S. National Stage of International Application No. PCT/KR2012/004421, filed Jun. 5, 2012, and claims priority to Korean Patent Application 10-2011-0112135, filed Oct. 31, 2011, the disclosures of which are herein incorporated by reference in their entirety.

TECHNICAL FIELD

The present invention relates to an implant for tissue lifting, and more particularly to an implant for tissue lifting that couples or integrates a mesh member having numerous pores on a distal portion of a bioimplantable thread, in one body, to facilitate smoothing of sagged or wrinkled skin.

BACKGROUND ART

Skin of a face or a neck generally experience reduced elasticity due to aging and stress, and sagging and wrinkling of skin or subcutaneous tissue of the face or neck occur in specific portions of or in the entire face or neck.

Accordingly, facial plastic surgeries for lifting sagged skin or subcutaneous tissue are commonly performed for aesthetic reasons or for correcting an asymmetry caused by facial nerve palsy.

A face lifting is one of the surgeries for smoothing wrinkles by pulling the wrinkled skin or subcutaneous tissue of the face or neck, and is categorized into a conventional face lifting, also referred to as an invasive face lifting that involves cutting and lifting sagged tissue through a visible incision, and a non-invasive face lifting that involves a simple surgery using a special thread, or the like.

The conventional face lifting has a range of incision starting from upper portions of ears, frontal portions of the ears, and rear portions of the ears, which leaves a great amount of scars on a patient and a long recovery period after a surgery. Also, despite the invasiveness of the surgery, there is a limitation on the effects on naso-labial fold or wrinkles near mouth, that is, on a distal portion being pulled for smoothing the wrinkles.

Recently, to overcome these problems, a simple tissue lifting using a medical thread or mesh, or the like is being widely performed.

In this regard, an GRAFT having a mesh shape or formed of a porous material, an GRAFT such as a bioimplantable thread having minute pores or cogs, and an inserting device for implanting the implant are disclosed in Korean Patent Publication No. 2010-0134941, Korean Patent Publication No. 2007-0093256, Korean Patent Publication No. 2007-0048178, Korean Patent Publication No. 2010-0058650, Korean Patent No. 10-0724706, Korean Patent No. 10-0886757, Korea Utility Model No. 20-0442490, International Publication No. WO2005/096956, and the like.

A thread lifting using a medical thread involves forming minute cogs or barbs on a synthetic thread and pulling the medical thread while the medical thread is inserted under the skin.

In addition to disuniformly pulling only certain portions of the tissue by pulling in a line instead of a face, thereby reducing effects of a tissue lifting, the thread lifting has other disadvantages such as damage of cogs, and the medical thread escaping from the tissue. Also, the cogs are unable to naturally pull tissues surrounding a surgical area and only pull at one point of the tissue, thereby reducing adhesion between the medical thread and the tissue, damaging the tissue, for example, by tearing the tissue apart, and resulting in an unnatural surgery.

Also, a conventional thread used in the tissue lifting has problems such as looseness after the surgery because the cogs of the conventional thread slip inside the tissue, reduced effects of the surgery caused by a low fixing strength of the conventional thread, leading to a loss of adhesion between the conventional thread and the tissue when muscle moves, and reduced pulling effects as the cogs are damaged when a great amount of tension is applied after surgery.

Also, the thread lifting using the conventional thread may lose the fixing strength fixing the distal portion, which is a main cause of actual wrinkles. In other words, in the case of a naso-labial fold, a fixing strength for lifting and fixing sagged tissue near the upper portion of the naso-labial fold is lost, thereby leading to a recurrence of sagging and wrinkling.

Also, a tissue lifting using a band shaped mesh only is a complex surgery that may require an incision and a second surgery, and the band shaped mesh is difficult to remove after the surgery, thereby causing inconveniences to patients. Accordingly, the tissue lifting using the band shaped mesh only is limitedly performed. Also, the tissue lifting using the band shaped mesh only has problems such as damaging tissues during the surgery.

Meshes used in surgeries of hernia and urinary incontinence must reduce adhesion to organs and be tension free. However, a mesh used in the tissue lifting must pull up a tissue that constantly sags due to the progress of aging, maintain tensile strength to resist muscle movements and traumas, and have firm adhesion to the tissue. Thus, since the meshes used in the surgeries of hernia and urinary incontinence and the mesh used in the tissue lifting have different requirements, the meshes used in the surgeries of hernia and urinary incontinence are difficult to be used in the tissue lifting.

DETAILED DESCRIPTION OF THE INVENTION

Technical Problem

The present invention provides an implant for a tissue lifting that couples or integrates a mesh member having a biocompatible material on a distal portion of a bioimplantable thread, in one body, to facilitate smoothing of sagged or wrinkled skin.

The present invention also provides an implant that is manufactured by coupling or integrating a mesh member having a predetermined shape to a bioimplantable thread to facilitate a firm lifting of the tissue.

Also, the present invention enables a tissue in a surgical area to grow and adhere to the mesh member located in the distal portion, which is an area of tissue that needs to be pulled, to firmly pull sagged tissue in the area just above the wrinkle, thereby reducing a recurrence of sagging.

Also, the present invention enables tissues surrounding the surgical area to adhere to the mesh member to form natural pulling of the tissue, and reduces damages to cogs and damages to tissues surrounding the cogs by reducing damages to the cogs even when tension applied to the bioimplantable thread increases, and increases fixing strength of tissues adhering to the mesh member, thereby facilitating an efficient tissue lifting.

Also, the present invention provides an implant having a loop shaped mesh member that is formed of a net shaped implant material exhibiting a suitable expansion rate, and maintains a uniform tension, thereby easily restoring back to the original shape, naturally moves along with movements such as facial muscle movements due to tissue ingrowth, and alleviates foreign body sensation.

Also, the present invention uses an implant that couples or integrates the bioimplantable thread and the mesh member, for tissue lifting, thereby reducing inconveniences to a patient during the surgery. When a removal is needed, the mesh member located at the distal portion may be easily caught by a removing tool, unlike in the tissue lifting using the existing thread, thereby facilitating a removal of the mesh member.

Also, the present invention uses a biocompatible material that is harmless to a human body, thereby preventing side effects after the surgery and alleviating foreign body sensation.

Also, in the present invention, a structure of the mesh member may be manufactured in various forms such that an adhesion between the tissue in the surgical area and the mesh member may improve up to a desired level, and the mesh member may couple to the bioimplantable thread regardless of a number of the mesh members, thereby improving the effects of the surgery.

Also, in the present invention, the mesh member coupled to the bioimplantable thread may be inserted between sagged or wrinkled skin and a subcutaneous muscle layer other than a facial area, thereby increasing an adhesion to the tissues and facilitating pulling and smoothing of the sagged and wrinkled skin and the subcutaneous tissue.

Also, in the present invention, the implant may be manufactured in a number and a size such that the cogs do not greatly reduce the adhesion caused by the mesh member and tissue ingrowth after an implantation, and thus the tensile strength of the thread may not be greatly reduced, unlike general incisive cogs.

Also, in the present invention, the cogs adhered to the implant not only support an initial anchoring strength, but also prevent movements of the mesh member and disperse the tension applied to the mesh member.

Technical Solution

According to an aspect of the present invention, there is provided an implant 2 for tissue lifting that is inserted between sagged or wrinkled skin s and subcutaneous muscle m to pull or smooth tissue. The implant 2 for a tissue lifting may include a bioimplantable thread 6 inserted between the skin s and the subcutaneous muscle m and having a distal portion where pulling is required and a proximal portion that is pulled; a mesh member 4 fixedly coupled to the distal portion of the bioimplantable thread 6 and having a plurality of pores, that are filled as bodily tissues grow.

According to an aspect of the present invention, there is provided an implant 2 for a tissue lifting that is inserted between wrinkled skin s and subcutaneous muscle m to pull and smooth tissue. The implant 2 for tissue lifting may include a bioimplantable thread 6 inserted between the skin s and the subcutaneous muscle m having a distal portion where puling is required and a proximal portion that is pulled; and a mesh member 4 integrally formed as one body with the bioimplantable thread 6 at the distal portion of the bioimplantable thread 6, wherein the mesh member 4 has a plurality of pores that are filled as bodily tissues grow.

According to an aspect of the present invention, there is provided an graft for tissue lifting 2 that is inserted between the skin s and the subcutaneous muscle m, is fixedly coupled to a bioimplantable thread 6 having a distal portion where pulling is required and a proximal portion where the bioimplantable thread 6 is pulled, and is formed as an integrated body with the bioimplantable thread 6 on the distal portion of the bioimplantable thread 6, and includes a mesh member 4 that has numerous pores, wherein bodily tissues may grow and fill the pores.

Cogs 8 may be formed on the bioimplantable thread 6.

The mesh member 4 may be cylindrical or flat.

The bioimplantable thread 6 may pass through the mesh member 4 while extending from both ends of the mesh member 4 to a certain length.

Both ends of the mesh member 4 may be fixedly coupled to the bioimplantable thread 6.

The bioimplantable thread 6 and the mesh member 4 may be coupled with each other by any one method of heat bonding, knotting, and using a medical adhesive material.

The bioimplantable thread 6 and the mesh member 4 of the implant 2 for tissue lifting may be integrated through an injection molding.

The bioimplantable thread 6 may have a thickness of about 0.25 mm to about 1.5 mm, which is a thickness that secures safety of the surgery while not showing external marks of the surgery.

The bioimplantable thread 6 may include a cogged portion t where cogs 8 protrude from a surface of the bioimplantable thread 6 in a certain direction, and a cogless portion r that integrally connects to the cogged portion and omits cogs 8 to be fixed on fascia.

The cogged portion t may include a removing portion that penetrates and pulls the skin when adjusting a lifting on a surface coupled to the mesh member, wherein the removing portion has a length within a range of about 15 mm to about 25 mm, which is a length for facilitating a partial removal of the removing portion after tissue lifting.

The cogged portion t may have a size of a space between adjacent cogs 8 in a range of about 2 mm to about 4 mm, and when the cogs 8 are incisive cogs, a depth of incision may be 25% or less of the diameter of the bioimplantable thread 6, and an angle of incision may be 10° or less.

The cogs 8 of the cogged portion t may be arranged in a spiral form on the surface of the bioimplantable thread 6 to distribute support strength.

The mesh member 4 may be formed by knitting or injection molding.

The mesh member 4 may be heat treated to maintain tensile strength.

The mesh member 4 may be coupled at about 15 mm to about 25 mm behind a frontal portion of the removing portion a to adjust pulling of the mesh member.

When the mesh member 4 is cylindrical, a length of the mesh member 4 may be about 15 mm to about 60 mm, an external diameter may be about 3.0 mm to about 4.5 mm, and a diameter of the hole of the mesh member h may be about 1 mm to about 2 mm to improve adhesion to the tissue and improve support strength.

When the mesh member is flat, a length of the mesh member may be about 15 mm to about 60 mm, a width may be about 3.0 mm to about 4.5 mm, and a diameter of the hole h of the mesh member 4 may be about 1 mm to about 2 mm.

The implant 2 for tissue lifting may include bioabsorbable medical polymer materials such as polydioxanone, poly-(l-lactic) acid, polyglycolic acid, polycaprolactone and a copolymer thereof that are harmless to a human body and are absorbed in vivo over time, or biocompatible medical polymer materials including polypropylene and a mixture thereof.

The bioimplantable thread 6 and the mesh member 4 may be coupled by repeating a process of inserting the bioimplantable thread 6 from the top to the bottom of a hole h of a flat mesh member 4, which has a prescribed surface size, and then inserting the bioimplantable thread 6 from the bottom to the top of another hole h of the flat mesh member 4, to penetrate the bioimplantable thread 6 through the mesh member 4.

The bioimplantable thread 6 may have a length of about 120 mm to about 230 mm to expose a portion the bioimplantable thread 6, and a guiding portion (g) that extends without the cogs 8 on a surface of the bioimplantable thread 6 to guide a penetration of the bioimplantable thread 6 that is inserted into an inserting cannula 20h.

A surgery may be performed by using the implant 2 for tissue lifting that is inserted into the tissue by using an inserting device 20 and a thread guiding needle 23 that hooks onto the guiding portion g of the bioimplantable thread 6 by using a hole formed on a surface or another surface to penetrate the inserting cannula 20h, wherein the inserting device 20 includes the inserting cannula 20h having a length of about 140 mm to about 250 mm, an external diameter of about 1.6 mm to about 2.8 mm, and an internal diameter of about 1.3 mm to about 2.5 mm, and a guide needle 22 having a length of about 145 mm to about 255 mm, and a diameter of about 1.2 mm to about 2.4 mm.

Advantageous Effects

An implant for tissue lifting of the present invention has an effect of improving adhesion to tissues in a surgical area or to tissues in surrounding areas by inserting a mesh member having a certain shape that is coupled to a bioimplantable thread into subcutaneous tissue.

Also, the implant for tissue lifting of the present invention provides an implant for tissue lifting where the mesh member having a certain shape is coupled to the bioimplantable thread to facilitate removal of wrinkles and lifting sagged tissues.

Also, the implant for tissue lifting of the present invention enables a natural lifting of the sagged tissue and the tissues in surrounding areas simultaneously, and preventing side effects such as a dimple phenomenon in the surgical area, thereby satisfying both a patient and a doctor.

Also, the implant for tissue lifting of the present invention increases fixing strength by an adhesion between a mesh member and tissue at a distal portion of the bioimplantable thread, thereby substantially reducing a recurrence of sagging.

Also, the implant for tissue lifting of the present invention includes the mesh member including a biocompatible material such as polypropylene that is not rejected from a human body and does not have side effects. Thus, the implant may be used semi-permanently.

Also, in the implant for tissue lifting of the present invention, since outer edges of the mesh member are formed in a loop-shape or in other smooth curvatures, the mesh member has light weight yet optimal expansibility. Also, the mesh member induces tissue ingrowth into pores of the mesh member after an implantation, thereby harmonizing with movements of facial muscles, alleviating foreign body sensation, and increasing patient satisfaction.

Also, the implant for tissue lifting has a monofilament as the mesh member and all pores of the mesh member maintain a size for a sufficient transmission of macrophages and neutrophils, thereby reducing a risk for an infection.

Also, the implant for tissue lifting has the bioimplantable thread that takes on most of the tension, and the bioimplantable thread has an integrated form with the mesh member as the bioimplantable thread passing through the mesh member takes on the tension, and a heat-treated mesh member is used to maintain an optimal tensile strength, thereby reducing a size of the mesh member compared to that of a conventional implant and reducing transformations such as rolling, folding, and string formation, despite changes in the tension, and maintaining desired functions of the mesh member.

Also, the implant for the tissue lifting has the bioimplantable thread that takes on most of the tension while the bioimplantable thread passes through the mesh member, not only reducing changes in pores of the mesh member but also enabling a use of a material that is light weight and capable of maintaining a pore size of at least 1 mm after the implantation, thereby reducing fibrotic bridging and a shrinkage of the mesh member caused by the fibrotic bridging, and reducing foreign body sensation.

Also, the implant for tissue lifting may enable an optimal adhesion between the mesh member located in the distal portion and the tissue, solving problems in a conventional surgery by preventing the recurrence of sagging in the distal portion and a recurrence of wrinkling due to the sagging, thereby improving effects of the surgery and substantially reducing dissatisfaction of the patient after the surgery.

Also, the implant for tissue lifting may also pull on surrounding tissues adhered to the mesh member, thereby naturally and stably maintaining lifting of the tissues compared to a thread lifting that pulls by using the bioimplantable thread only.

BEST MODE

Figure 1:
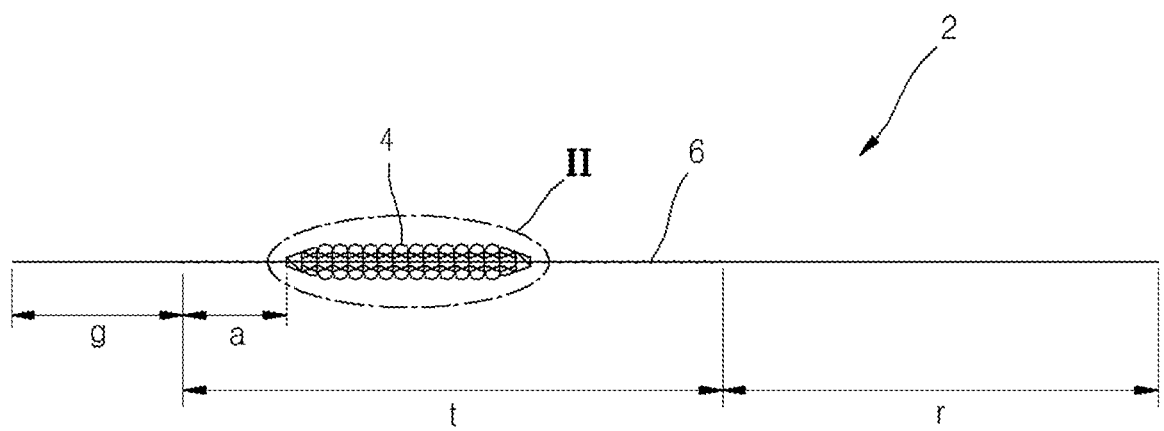
FIG. 1 illustrates an implant for tissue lifting according to an embodiment of the present invention.
Figure 2:
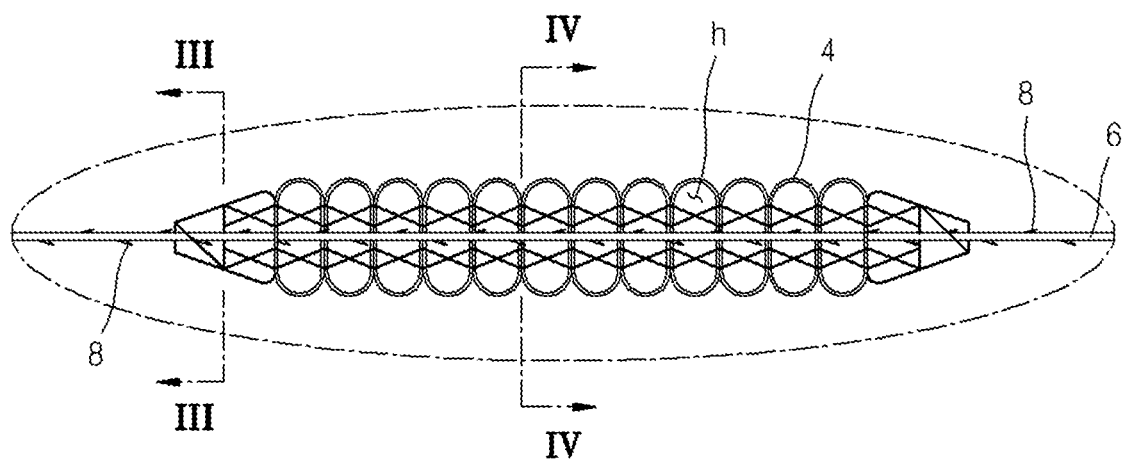
FIG. 2 is a partially enlarged view of FIG. 1.

Hereinafter, embodiments of the present invention are described with reference to the accompanying drawings.

Embodiment 1

An implant 2 for tissue lifting according to an embodiment of the present invention is inserted between sagged or wrinkled skin s and a subcutaneous muscle layer m to enable pulling or smoothing of tissue. As illustrated in FIGS. 1 to 4, the implant 2 for tissue lifting includes a bioimplantable thread 6 having cogs 8 on a surface of the bioimplantable thread 6 and a mesh member 4 that is coupled to the bioimplantable thread 6, both ends of the mesh member 4 being fixed by the bioimplantable thread 6 extended to have extra lengths on both ends.

The bioimplantable thread 6 may be inserted between skin and the subcutaneous muscle layer, and may have a distal portion (an area provided at wrinkled skin) that is being pulled, and a proximal portion (an end of a cogless portion r) that is a pulling portion. Here, the distal portion refers to a portion provided at the sagged or wrinkled skin, and the proximal portion refers to a portion pulling on the distal portion.

Here, the bioimplantable thread 6 has a thickness of about 0.25 mm to about 1.5 mm, which is a thickness that secures safety of the surgery while not showing external marks of the surgery, and includes a cogged portion t where the cogs 8 protrude from a surface of the bioimplantable thread 6 in a certain direction, and the cogless portion r that is located on the other side of the cogged portion t and may be fixed on fascia by omitting the cogs 8.

The cogged portion t may include a removing portion a formed at one side of the mesh member and has a length within a range of about 15 mm to about 25 mm, which is a length for penetrating and pulling the skin s when adjusting a lifting and facilitating a removal when the mesh member 4 has been secured or fixed in a desired area.

Also, a guiding portion (g) that has a length of about 120 mm to about 230 mm to expose a portion of the bioimplantable thread 6 inserted into an inserting cannula and extends from the removing portion a of the bioimplantable thread 6 to guide passing of the bioimplantable thread 6 inserted into the inserting cannula is provided at one side of the bioimplantable thread 6.

The bioimplantable thread 6 penetrates the mesh member 4 by extending certain lengths from both ends of the mesh member 4.

To form the cogs 8 of the cogged portion t on the bioimplantable thread 6, incision, heat pressing, injection molding, or the like may be used. Here, unlike a conventional bioimplantable thread having cogs, the cogs 8 may share the responsibility of tissue lifting with the mesh member 4 or take on an auxiliary function, and as a result, the bioimplantable thread 6 may be cogless or have cogs 8 at certain portions depending on conditions of the surgery. Even when there are the cogs 8, a size and a number of the cogs 8 may be reduced. Also, the cogs 8 may be arranged in a spiral form along a length direction of the bioimplantable thread 6 to facilitate a distribution of support strength.

Here, an interval between the adjacent cogs 8 of the cogged part t is between about 2 mm to about 4 mm. When the cogs 8 are incisive cogs, a depth of incision with respect to the bioimplantable thread 6 is 25% or less, and an angle of incision is 10° or less.

The mesh member 4 may be fixedly coupled to the distal portion of the bioimplantable thread 6 and have numerous holes h. Bodily tissues may grow and fill in the holes h. One end and the other end of the mesh member 4 may approximately form a triangle and numerous oval shaped holes may be attached to each other between the opposite ends.

The mesh member 4 may include a bioabsorbable medical polymer material such as polydioxanone, poly-(l-lactic) acid, polyglycolic acid, polycaprolactone and a copolymer thereof that are harmless to a human body and are absorbed in vivo over time, or a biocompatible medical polymer material including polypropylene and a mixture thereof. Here, the mesh member 4 is flat, and may be formed by knitting or by injection molding, and may be heat treated to maintain tensile strength.

The mesh member 4 may be inserted into one of face, neck, breast, and hip, and a size of a mesh may be enlarged or reduced depending on a size of the surgical area. Also, the number of the mesh does not need to be one, and there may be additional meshes depending on the need.

The mesh member 4 is provided at the rear portion of the removing portion a that has a length of about 15 mm to about 20 mm. Hence, the mesh member 4 may be coupled to about 15 mm to about 25 mm behind a leading portion of the removing portion a of the bioimpantable thread 6 to facilitate adjustment of pulling of the mesh member 4.

The mesh member 4 may have a length in a range of about 15 mm to about 60 mm, a width in a range of about 3.0 mm to about 4.5 mm, and a diameter of the hole h of about 1 mm to about 2 mm.

When the mesh member 4 is manufactured by knitting, both edges of the mesh member 4 may be gently rounded. When both edges of the mesh member 4 are gently rounded, damages to the tissue may be reduced.

Figure 3:
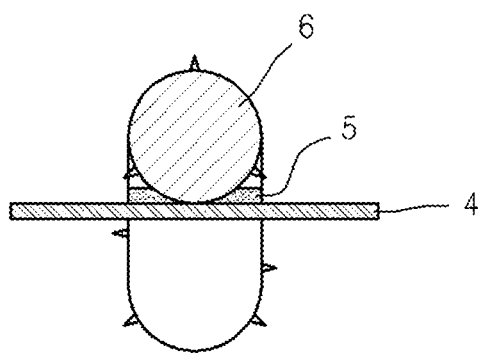
FIG. 3 is a cross-sectional view taken along the line III-Ill of FIG. 2.
Figure 4:
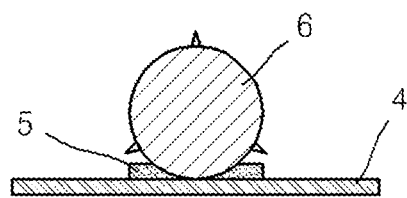
FIG. 4 is a cross-sectional view taken along the line IV-IV of FIG. 2.

In a method of coupling the bioimplantable thread 6 and both ends of the mesh member 4 as illustrated in FIG. 3, the bioimplantable thread 6 may be alternately inserted from the top and the bottom of the holes h of the mesh member 4, arranging the bioimplantable thread 6 in a zigzag form, and then coupling the mesh member 4 and the bioimplantable thread 6 by heat bonding, a medical adhesive material 5, or the like. Also, in a central area between both ends of the mesh member 4, while the bioimplantable thread 6 is located on the surface of the mesh member 4, the mesh member 4 and the bioimpantable thread 6 may be coupled with each other by heat bonding or the adhesive material 5 as illustrated in FIG. 4. A reason for different coupling methods used in both ends and the area between both ends of the mesh member 4 is because both ends of the mesh member 4 receive a greater force than the central area, thereby requiring a greater fixing strength.

Embodiment 2

Figure 5:
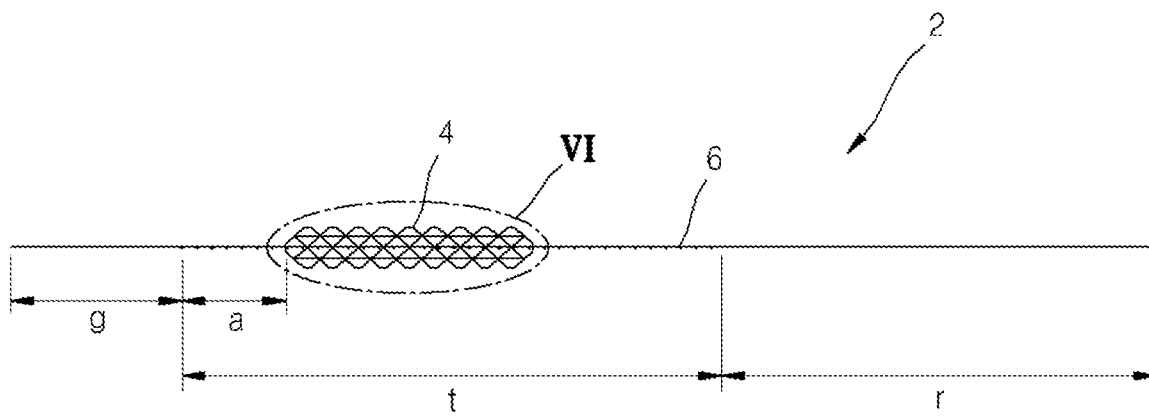
FIG. 5 illustrates an implant for tissue lifting according to another embodiment of the present invention.
Figure 6:
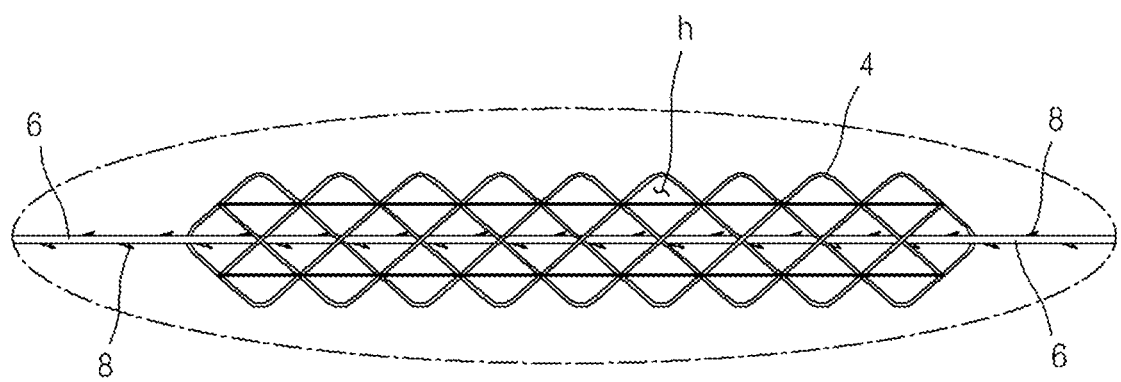
FIG. 6 is a partially enlarged view of FIG. 5.

The implant 2 for tissue lifting illustrated in FIGS. 5 and 6 has a substantially similar structure to that of Embodiment 1, except for a shape of overlapping rhombuses. Here, the implant 2 for tissue lifting illustrated in FIG. 5 also has the bioimplantable thread 6 coupled to both ends of the mesh member 4 in a zigzag form and placed on one surface of the mesh member 4 in the central area between both ends.

Embodiment 3

Figure 7:
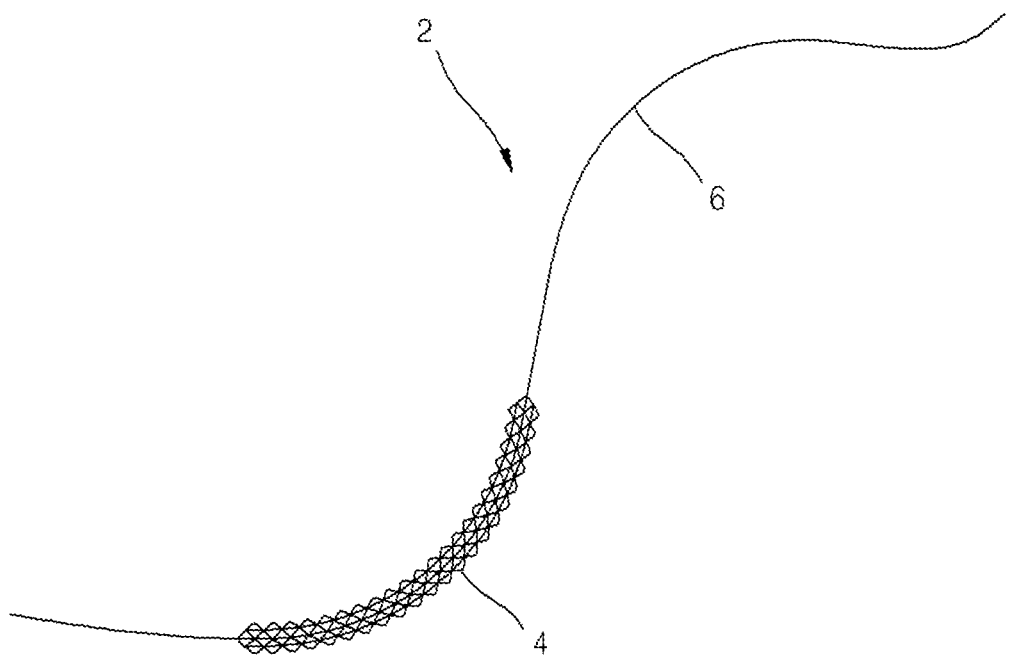
FIG. 7 illustrates an implant for tissue lifting according to another embodiment of the present invention.

The implant 2 for tissue lifting illustrated in FIG. 7 does not have any cogs on the bioimplantable thread 6, unlike the implant 2 for tissue lifting illustrated in FIGS. 1 to 4. Because the bioimplantable thread 6 of the implant 2 for tissue lifting does not have cogs, a length of the mesh member 4 is longer than the mesh member 4 illustrated in FIGS. 1 to 4, and the mesh member 4 obtains sufficient fixing strength, thereby preventing reduction in overall fixing strength even without the cogs.

Embodiment 4

Figure 8:
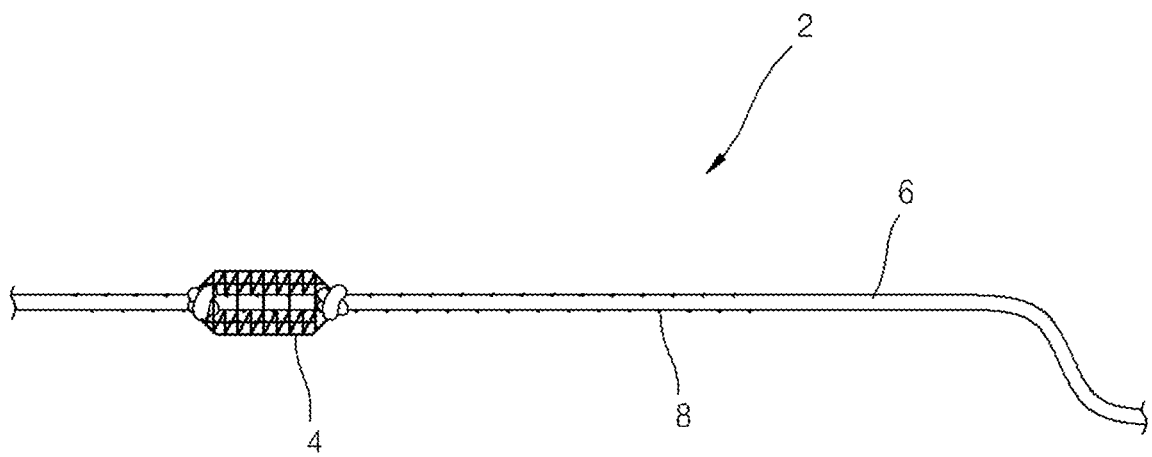
FIG. 8 illustrates an implant for tissue lifting according to another embodiment of the present invention.

The implant 2 for tissue lifting illustrated in FIG. 8 has the mesh member 4 coupled to the bioimplantable thread 6 by a knot, unlike the implant 2 for tissue lifting illustrated in FIGS. 1 to 4. Particularly, as both ends of the mesh member 4 are fixed by knotting, the mesh member 4 is certainly prevented from falling off from the bioimplantable thread 6.

Embodiment 5

Figure 9:
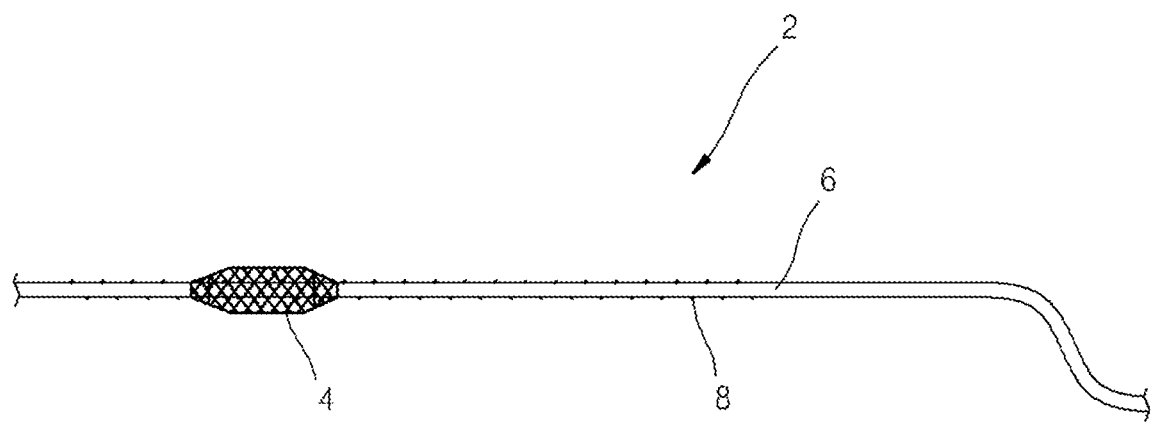
FIG. 9 illustrates an implant for tissue lifting according to another embodiment of the present invention.

The implant 2 for tissue lifting illustrated in FIG. 9, unlike the implant 2 for tissue lifting illustrated in FIGS. 1 to 4, has both ends of the mesh member 4 adhered to the bioimplantable thread 6 while both ends of the mesh member 4 are placed on one side of the bioimplantable thread 6. In other words, the bioimplantable thread 6 couple with the mesh member 4 simply by an adhesion instead of the bioimplantable thread 6 coupling with the mesh member 4 by the bioimplantable thread 6 alternately passing through the holes h of the mesh member 4 from the top and the bottom. Because the implant 2 for tissue lifting does not have the bioimplantable thread 6 coupled to both ends of the mesh member 4 in a zigzag form, the implant 2 for tissue lifting may be easily manufactured.

Embodiment 6

Figure 10:
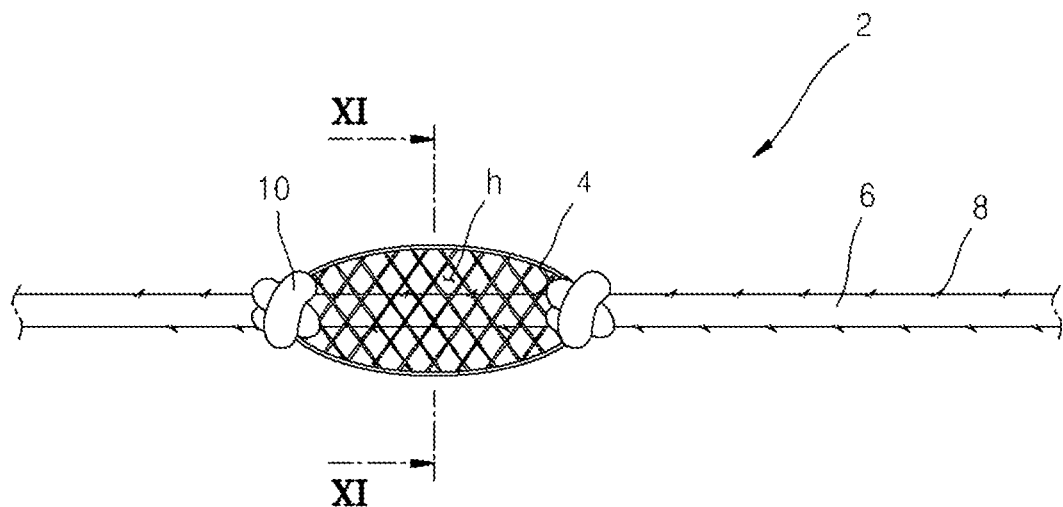
FIG. 10 illustrates an implant for tissue lifting according to another embodiment of the present invention.
Figure 11:
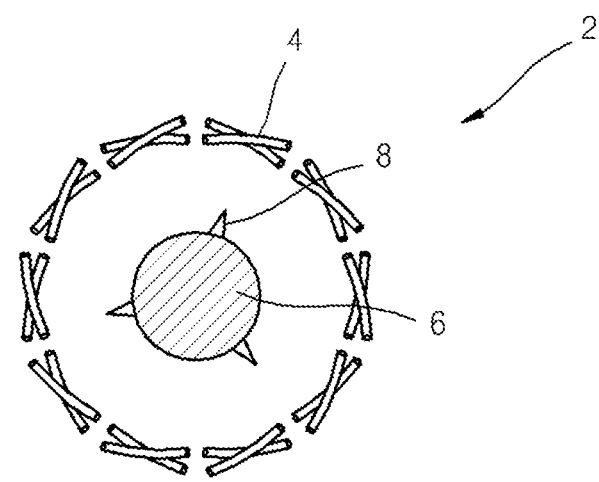
FIG. 11 is a cross-sectional view taken along the line XI-XI of FIG. 10.

The implant 2 for tissue lifting illustrated in FIGS. 10 and 11 has the mesh member 4 that is cylindrical. The cylindrical mesh member 4 is provided by being tied to the bioimplantable thread 6 forming the knot 10 at the rear of the removing portion a having a length of about 15 mm to about 20 mm from a leading portion in an inserting direction of the bioimplantable thread 6 having the cogs 8 on a surface of the bioimplantable thread 6. In other words, the cylindrical mesh member 4 is coupled to the bioimplantable thread 6 while leaving the removing portion a on one end of the bioimplantable thread 6 to facilitate adjustment of pulling of the cylindrical mesh member 4. The cylindrical mesh member 4 has a length of about 15 mm to about 60 mm, an external diameter of about 3.0 mm to about 4.5 mm, and a diameter of a hole h of about 1.0 mm to about 2.0 mm so as to facilitate adhesion of the mesh member 4 to tissue and exertion of support strength.

Figure 12:
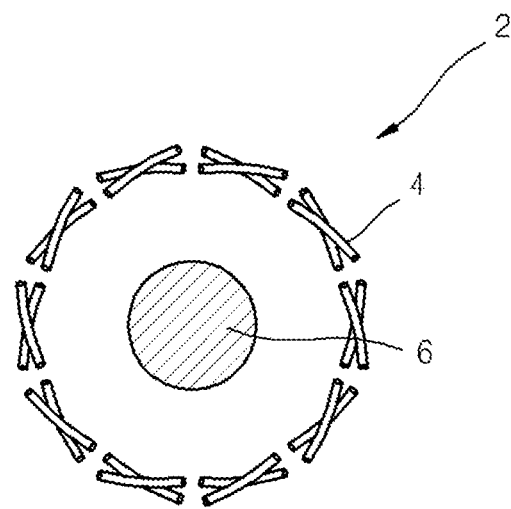
FIG. 12 is a cross-sectional view of an implant for tissue lifting according to another embodiment of the present invention.

The implant 2 for tissue lifting illustrated in FIG. 12 has a shape almost similar to the implants 2 for tissue lifting in FIGS. 10 and 11. However, the bioimplantable thread 6 passing through the mesh member 4 in FIG. 12 does not have cogs on the surface of the bioimplantable thread 6.

Embodiment 7

Figure 13:
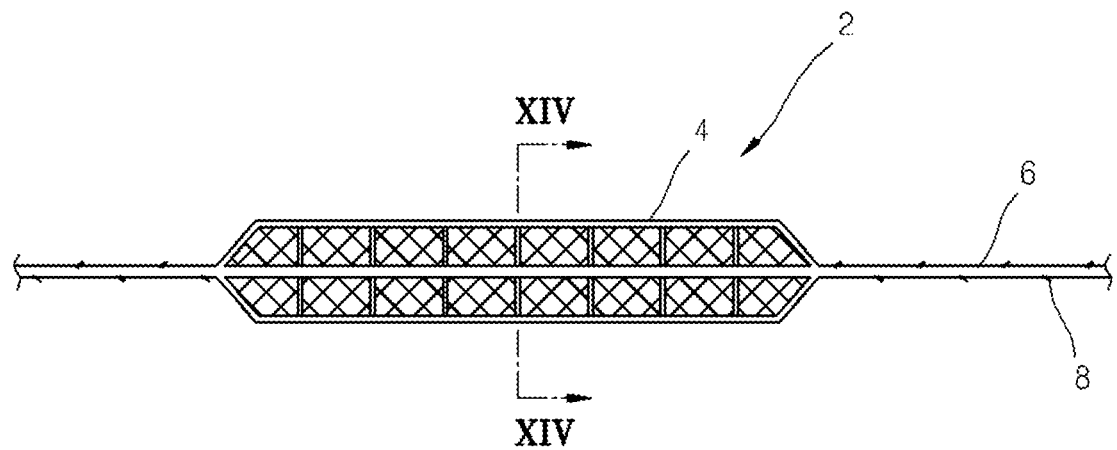
FIG. 13 illustrates an implant for tissue lifting according to another embodiment of the present invention.
Figure 14:
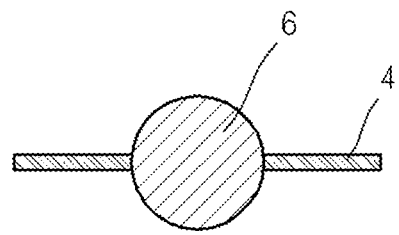
FIG. 14 is a cross-sectional view taken along the line XIV-XIV of FIG. 13.

Unlike the implant 2 for tissue lifting illustrated in FIGS. 1 to 4, the implant for tissue lifting 2 illustrated in FIGS. 13 and 14 is manufactured not by coupling a biological mesh member and a bioimplantable thread that are separately formed, by using a bond or a knot, but by integrally forming the mesh member 4 and the bioimplantable thread 6 in one body. Here, the mesh member 4 and the bioimplantable thread 6 are integrally formed as one body by an injection molding. As the mesh member 4 and the bioimplantable thread 6 are integrally formed as one body by using an identical material, the mesh member 4 and the bioimplantable thread 6 are advantageous in that the mesh member 4 and the bioimplantable thread 6 are not easily separated from each other and may expand to the same extent.

Figure 15:
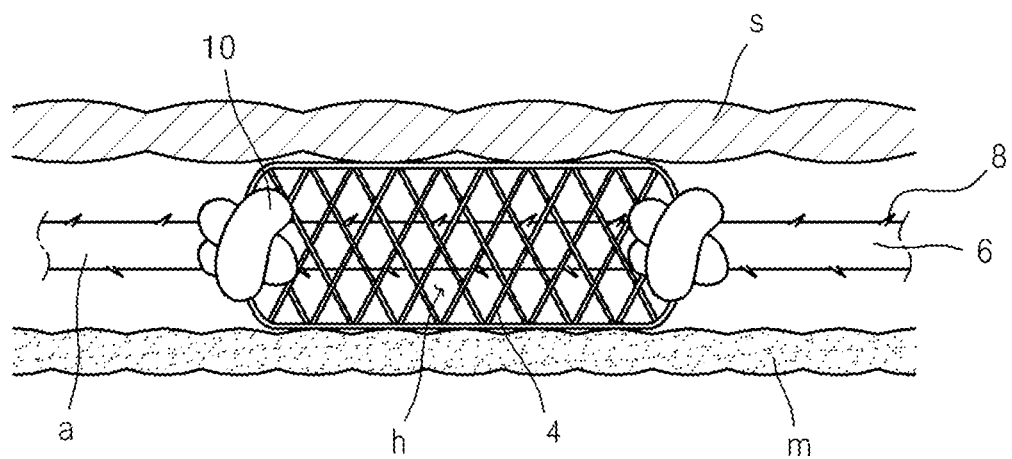
FIG. 15 is an enlarged view of an implant for tissue lifting according to the present invention provided between skin and subcutaneous muscle.

The implant 2 for tissue lifting of the present invention described above is inserted in tissue between skin s and subcutaneous muscle m to lift the tissue, as illustrated in FIG. 15.

Hence, the skin s and the subcutaneous tissue m after a surgery grow into the holes h of the mesh member 4, and as the skin s and the subcutaneous tissue m experience tissue ingrowth, the skin s and the subcutaneous tissue m fill the holes h of the mesh member 4 and are adhered to the mesh member 4.

Figure 16:
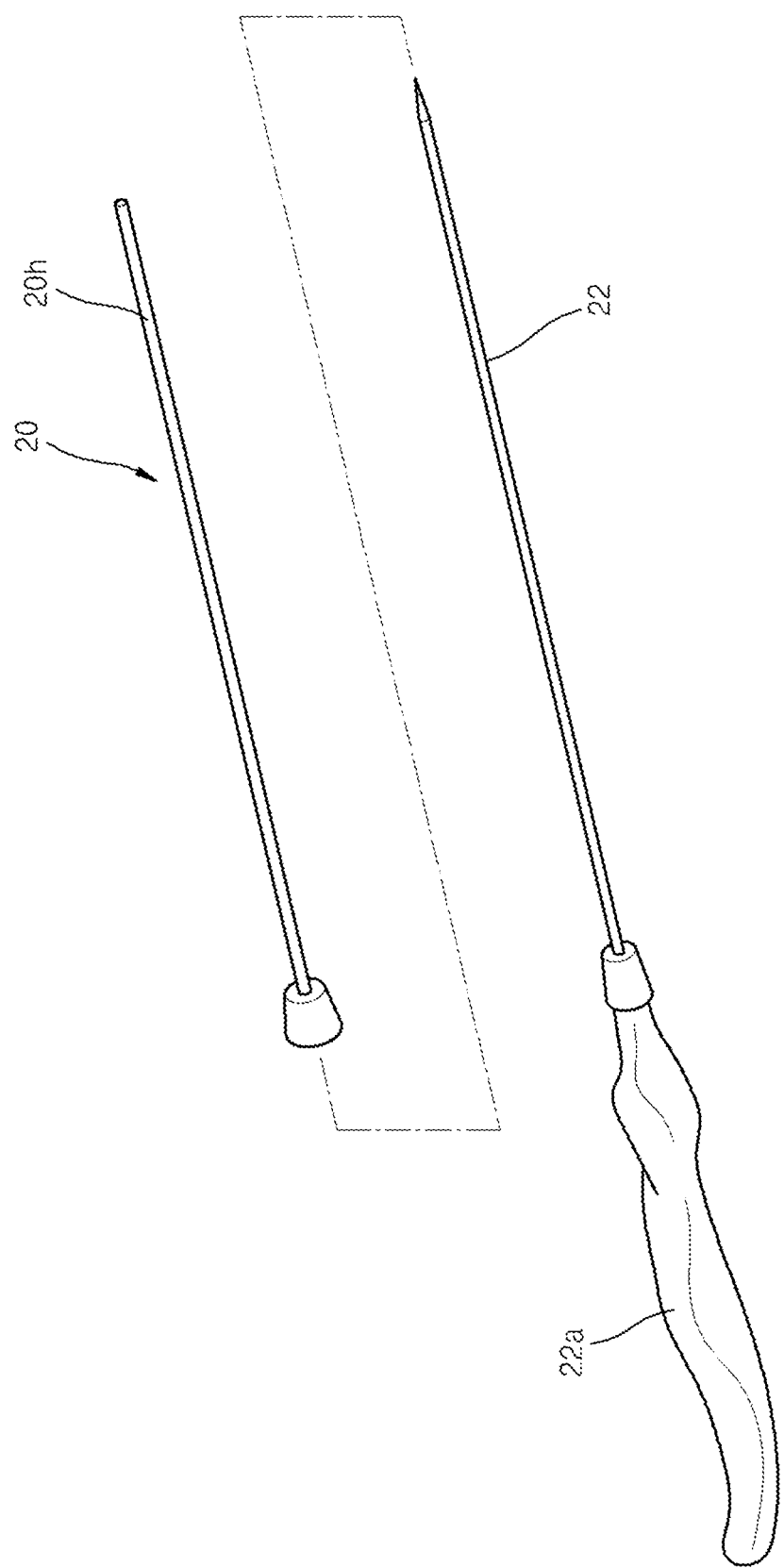
FIG. 16 illustrates an inserting device for inserting an implant for tissue lifting according to the present invention.

Also, an inserting device 20 illustrated in FIG. 16 facilitates an insertion of the implant 2 for tissue lifting and an operation, and includes an inserting cannula 20h and a guide needle 22. The inserting cannula 20h has a length of about 140 mm to about 250 mm, and has an external diameter of about 1.6 mm to about 2.8 mm and an internal diameter of about 1.3 mm to about 2.5 mm to facilitate insertion of the implant 2 for tissue lifting.

The guide needle 22 has a length of about 145 mm to about 255 mm and a diameter of about 1.2 mm to about 2.4 mm to facilitate insertion between the skin s and the subcutaneous muscle m, and has a pointy leading portion that protrudes from an end of the inserting cannula 20h, thereby facilitating the insertion of the inserting cannula 20h between the skin s and the subcutaneous muscle m. A handle 22a is formed at the rear portion of the guide needle 22.

Figure 17:
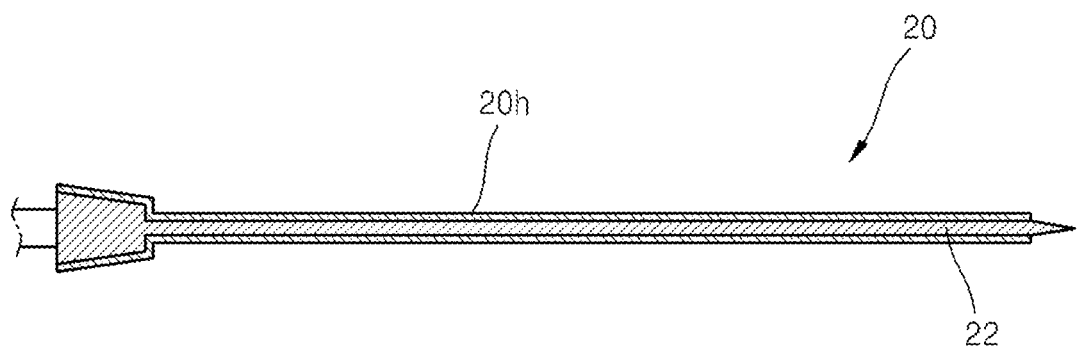
FIG. 17 is a cross-sectional view illustrating an assembled state of FIG. 16.
Figure 18:
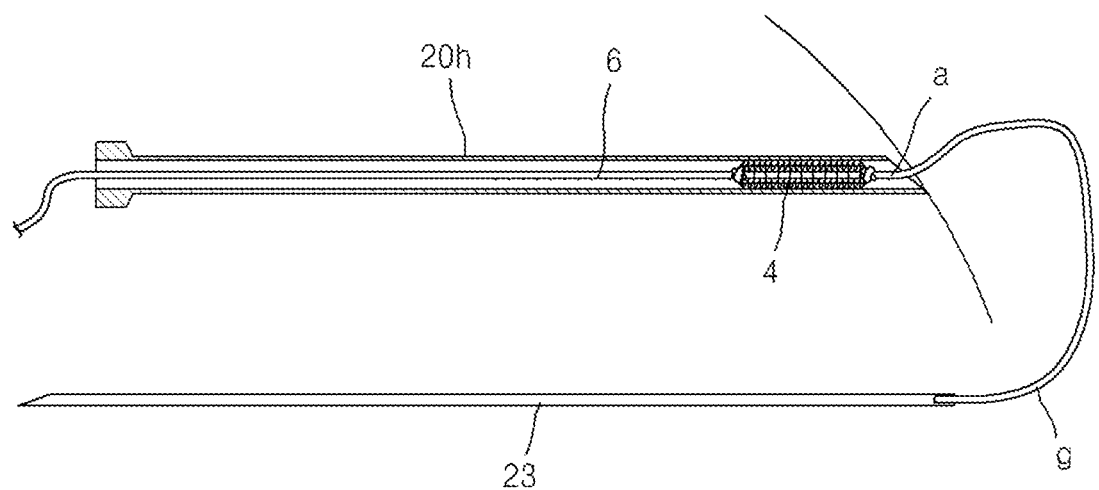
FIG. 18 illustrates an implant for tissue lifting according to the present invention inserted in an inserting device.

Also, after inserting the inserting device 20 illustrated in FIG. 17 between the skin s and the subcutaneous muscle m, the guide needle 22 is taken out from the inserting cannula 20h, and a thread guiding needle 23 is inserted into the inserting cannula 20h as illustrated in FIG. 18. Here, the thread guiding needle 23 plays a role of hooking a guiding portion g of the bioimplantable thread 6, passing the same through the inserting cannula 20h, and piercing out of a predetermined area of the skin.

Also, the mesh member 4 coupled to the bioimplantable thread 6 enables a firm adhesion to fibrotic tissues, thereby smoothing the wrinkled skin and lifting the sagged skin.

Figure 19:
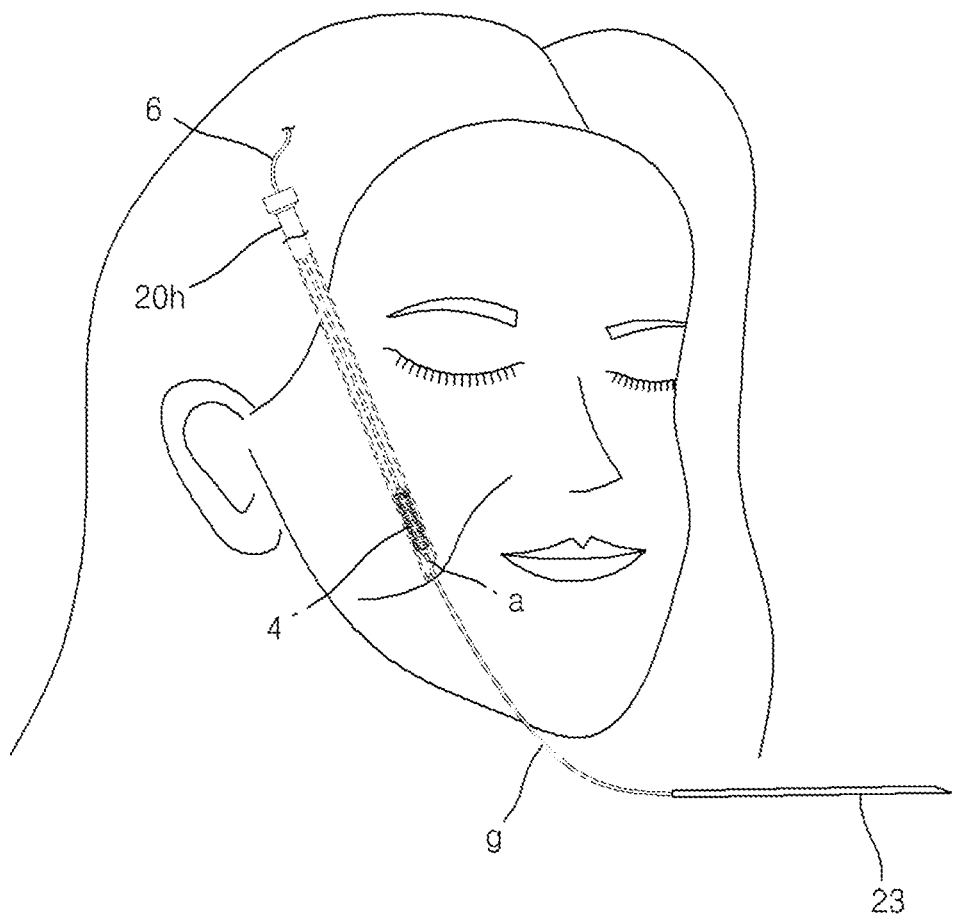
FIG. 19 illustrates an implant for tissue lifting according to the present invention provided between skin and subcutaneous muscle by an inserting device.
Figure 20:
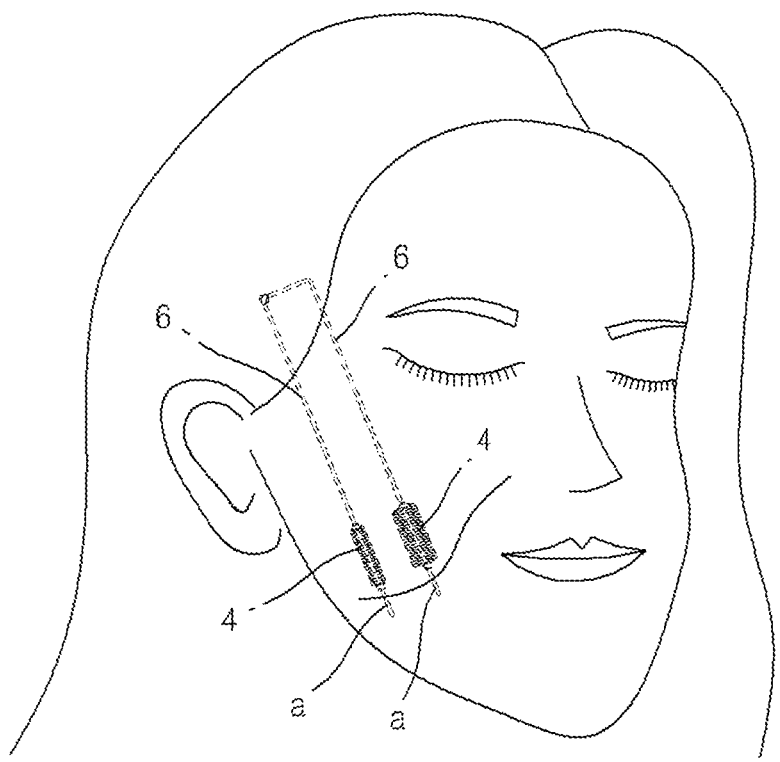
FIG. 20 illustrates an example of a facial lifting by fixing an implant for tissue lifting according to the present invention to be suspended in temporal fascia.

Hereinafter, a tissue lifting operation performed as described above by using the implant for tissue lifting will be described in detail with references to FIGS. 19 and 20.

First, the inserting device 20 is advanced through an incised area, until just before piercing the skin. Thereafter, only the guide needle 22 is removed while leaving the inserting cannula 20h intact, then the guiding portion g of the bioimplantable thread 6 is hooked onto the thread guiding needle 23, penetrating the thread guiding needle 23 through the inserting cannula 20h, and making the thread guiding needle 23 to pierce out of the predetermined area of the skin.

The guiding portion g protruding out of the skin is pulled such that the removing portion a of the bioimplantable thread 6 is exposed through the inserting cannula 20h. Thereafter, while holding the removing portion a of the bioimplantable thread 6 exposed out of the skin s, the inserting cannula 20h is retreated to be pulled out. Then, a pulling level is adjusted by holding the g and r separately to locate the mesh member 4 to a sagged area of the skin. After adjusting a pulling state by pulling the implant for the tissue lifting 2 inserted between the sagged or wrinkled skin s and the subcutaneous muscle m, the removing portion a of the bioimplantable thread 6 is partially removed as illustrated in FIG. 20. The surgery is completed when one end of the bioimplantable thread 6 is tied to another bioimplantable thread 6 of another implant 2 for tissue lifting operated in the same manner, such that two bioimplantable threads 6 forming the cogless parts r of the implants 2 for tissue lifting are fixed to fascia or the like forming a knot.

The implant 2 for tissue lifting inserted between the skin s and the subcutaneous muscle m is firmly adhered to the tissue as a tissue growing as time passes fills the holes h of the mesh member 4.

The mesh member 4 adheres not only on the surgical area but also on tissues surrounding the surgical area, thereby lifting the entire surgical area after the surgery over time and improving the effects of the face lifting.

Figure 21:
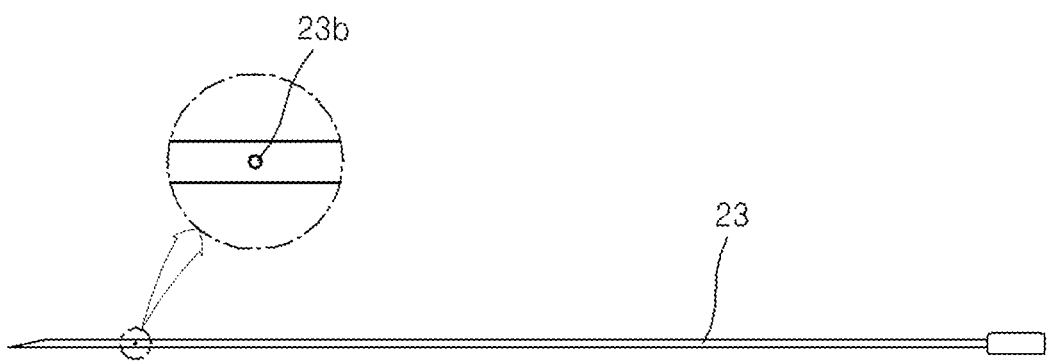
FIG. 21 illustrates a thread guiding needle guiding an implant for tissue lifting according to the present invention.

Also, the thread guiding needle 23 has a distal hole 23b where the bioimplantable thread 6 may hook such that the distal portion of the bioimplantable thread 6 hooks onto the thread guiding needle 23 as illustrated in FIG. 21, in addition to the bioimplantable thread hooking onto a proximal portion as illustrated in FIG. 18.

While the present invention has been described with reference to embodiments and embodiments in the drawings and the specification, but the present invention is not limited thereto and may be variously transformed according to the area where the present invention is being used for, and the present invention includes all implants for tissue lifting including a complex of a thread and a mesh member.

The invention claimed is:

1. An implant for tissue lifting comprising:
a bioimplantable thread configured to be inserted between skin and subcutaneous muscle and having a distal portion where pulling is required and a proximal portion that pulls on the distal portion; and
a mesh member having a plurality of pores, the mesh member having an outer perimeter,
wherein cogs are formed on the bioimplantable thread and the cogs protrude from a surface of the bioimplantable thread,
wherein the cogs on the bioimplantable thread are arranged to allow passage of the bioimplantable thread in a first direction through tissue and resist movement of the bioimplantable thread in a second direction and are configured to penetrate and pull tissue to facilitate tissue lifting,
wherein both ends of the mesh member are fixed to the surface of the bioimplantable thread such that the bioimplantable thread is configured to be linearly disposed within or adjacent to the mesh member,
wherein the mesh member has a first end portion, a central portion connected to the first end portion, and a second end portion connected to the central portion and disposed on an opposite side of the first end portion,
wherein the first end portion and the second end portion are tapered in a longitudinal direction of the mesh member and gradually thinning toward the respective both ends thereof,
wherein the central portion includes a plurality of oval-shaped elements arranged in a single row, each oval-shaped element extends from a first side of the outer perimeter to a second side of the outer perimeter opposite the first side, the plurality of pores are formed in the plurality of oval shaped elements, and the plurality of oval-shaped elements are attached to each other to be consecutively arranged along the bioimplantable thread.

2. The implant for tissue lifting of claim 1, wherein the bioimplantable thread and the mesh member are coupled with each other using a process selected from the group consisting of: heat bonding, knotting, using a medical adhesive material, and combinations thereof.

3. The implant for tissue lifting of claim 1, wherein the bioimplantable thread has a thickness of about 0.25 mm to about 1.5 mm, which is a thickness that secures safety of a surgery while not showing external marks of the surgery.

4. The implant for tissue lifting of claim 1, wherein the bioimplantable thread comprises a cogged portion where the cogs protrude from the surface of the bioimplantable thread, and a cogless portion separated from the mesh member that integrally connects to the cogged portion and omits the cogs to be fixed on fascia.

5. The implant for tissue lifting of claim 4, wherein the cogged portion comprises a removing portion that is configured to penetrate the skin and that is configured to be pulled after the removing portion penetrates the skin, wherein the removing portion has a length within a range of about 15 mm to about 25 mm.

6. The implant for tissue lifting of claim 5, wherein the mesh member is coupled at about 15 mm to about 25 mm behind a frontal portion of the removing portion to adjust a pulling of the mesh member.

7. The implant for tissue lifting of claim 4, wherein the cogged portion has a size of a space between adjacent cogs in a range of about 2 mm to about 4 mm, and when the cogs are incisive cogs, a depth of incision is 25% or less of a diameter of the bioimplantable thread.

8. The implant for tissue lifting of claim 4, wherein the cogs of the cogged portion are arranged in a spiral form on the surface of the bioimplantable thread to distribute support strength.

9. The implant for tissue lifting of claim 1, wherein the mesh member is formed by knitting or injection molding.

10. The implant for tissue lifting of claim 9, wherein the mesh member is heat treated to maintain tensile strength.

11. The implant for tissue lifting of claim 1, wherein the implant for tissue lifting comprises a bioabsorbable medical polymer material selected from polydioxanone, poly-(l-lactic) acid, polyglycolic acid, polycaprolactone and a copolymer thereof that are harmless to a human body and are absorbed in vivo over time, or a biocompatible medical polymer material comprising polypropylene and a mixture thereof.

12. The implant for tissue lifting of claim 1, wherein the bioimplantable thread of the implant for the tissue lifting has a length of about 120 mm to about 230 mm to expose a portion the bioimplantable thread, and a guiding portion separated from the mesh member that extends without the cogs on a surface of the bioimplantable thread for guiding a penetration of the bioimplantable thread being inserted into an inserting cannula.

13. The implant for tissue lifting of claim 1, wherein the cogs are also located on portions of the bioimplantable thread that extend from both ends of the mesh member.

14. The implant for tissue lifting of claim 1, wherein the cogs are arranged in a spiral form on the surface of the bioimplantable thread.

\* \* \* \* \*